US007118888B2

(12) United States Patent
Mohapatra et al.

(10) Patent No.: US 7,118,888 B2
(45) Date of Patent: Oct. 10, 2006

(54) GENE EXPRESSION VACCINE

(75) Inventors: Shyam S. Mohapatra, Tampa, FL (US); Mukesh Kumar, Norwood, MA (US); Shua-ku Huang, Towson, MD (US); Kam Leong, Ellicott City, MD (US)

(73) Assignees: University of South Florida Board of Trustees, Tampa, FL (US); Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/073,065

(22) Filed: Feb. 12, 2002

(65) Prior Publication Data

US 2003/0068333 A1 Apr. 10, 2003

Related U.S. Application Data

(60) Provisional application No. 60/325,573, filed on Sep. 28, 2001.

(51) Int. Cl.
*C12P 21/06* (2006.01)

(52) U.S. Cl. .................. 435/69.1; 435/69.5; 435/69.7; 435/235.1; 435/236; 435/239; 435/455; 435/320.1; 424/93.2; 424/187.1; 424/185.1; 424/186.1; 424/202.1; 424/204.1; 424/211.1; 424/234.1; 424/489; 424/490; 424/491; 514/2; 514/8; 514/44; 514/55; 530/300; 530/350; 536/23.1; 536/23.7; 536/23.72; 536/20

(58) Field of Classification Search .............. 424/93.2, 424/187.1, 195.1, 186.1, 202.1, 204.1, 211.1, 424/234.1, 278.1, 184.1, 489, 490, 491, 185.1; 514/2, 8, 44, 55; 435/69.1, 69.5, 69.7, 235.1, 435/236, 239, 455, 320.1; 536/23.72, 20, 536/23.7, 23.1; 530/300, 390, 850
See application file for complete search history.

(56) References Cited

U.S. PATENT DOCUMENTS

| | | | | |
|---|---|---|---|---|
| 5,882,651 | A * | 3/1999 | Murphy et al. | 424/211.1 |
| 6,184,037 | B1 * | 2/2001 | Rolland et al. | 435/455 |
| 6,264,957 | B1 * | 7/2001 | Collins | 424/211.1 |
| 6,489,306 | B1 | 12/2002 | Mohapatra et al. | |
| 6,900,299 | B1 | 5/2005 | Mohapatra et al. | |
| 2001/0006951 | A1 | 7/2001 | Mohapatra et al. | |
| 2003/0198624 | A1 | 10/2003 | Mohapatra et al. | |
| 2005/0159385 | A1 | 7/2005 | Mohapatra | |
| 2005/0266093 | A1 | 12/2005 | Mohapatra | |
| 2005/0272650 | A1 | 12/2005 | Mohapatra | |

FOREIGN PATENT DOCUMENTS

| | | | |
|---|---|---|---|
| GB | WO 90/09780 | * | 9/1990 |
| WO | WO85/04185 | * | 7/1987 |
| WO | WO 97/20576 A1 | | 6/1997 |
| WO | WO 98/02457 | * | 1/1998 |
| WO | WO 98/02457 A1 | | 1/1998 |
| WO | WO 99/36089 A1 | | 7/1999 |
| WO | WO 02/34287 A2 | | 5/2002 |
| WO | WO 02/44334 A2 | | 6/2002 |
| WO | WO 03/028759 A1 | | 4/2003 |

OTHER PUBLICATIONS

Stedman's Online Medical Dictionary, 27th Ed, home http://www.stedmans.com, 2003-definition "antigen".*
Leong et al., Journal of Controlled Release, vol. 53, pp. 183-193 (1998).*
Collins et al., Proceedings of the National Academy of Sciences, USA, vol. 92, pp. 11563-11567 (1995).*
HSu et al., Journal of General Virology, vol. 80, pp. 1401-1405 (1999).*
Simmons et al., Journal of Immunology, vol. 166 No. 2, pp. 1106-1113 (Jan. 2001).*
Wright et al., Journal of Infectious Diseases, vol. 182 No. 5, pp. 1331-1342 (Sep. 2000).*
Montgomery et al., Pharmacology and Therapeutics, vol. 74 No. 2, pp. 195-205 (1997).*
Pastey et al., Journal of General Virology, vol. 76 No. 1, pp. 193-197 (Jan. 1995).*
Chanock et al.,, "Serious Respiratory Tract Disease Caused by Respiratory Syncytial Virus: Prospects for Improved Therapy and Effective Immunization", Pediatrics, 1992, pp. 137-141.
Roy et al., "Oral Gene Delivery With Chitosan-DNA Nanoparticles Generates Immunologic Protection in a Murine Model of Peanut Allergy", Nature Medicine, 1999, pp. 387-390.
Behera et al., "Blocking Intercellular Adhesion Molecule-1 on Human Epithelial Cells Decreases Respiratory Syncytial Virus Infection", 2001, pp. 188-195.
Matsuse et al., "Recurrent Respiratory Syncytial Virus Infections in Allergen-Sensitized Mice Lead to Persistent Airway Inflammation and Hyperresponsiveness", 2000, pp. 6583-6592.

(Continued)

*Primary Examiner*—Bruce R. Campell
*Assistant Examiner*—Myron G. Hill
(74) *Attorney, Agent, or Firm*—Saliwanchik, Lloyd & Saliwanchik

(57) ABSTRACT

An effective prophylactic mucosal gene expression vaccine (GXV), made up of a cocktail of at least 4 different plasmid DNAs encoding corresponding RSV antigens, coacervated with chitosan to formulate nanospheres. In a murine model of RSV infection, intranasal administration with GXV results in significant induction of RSV-specific antibodies, nasal IgA antibodies, cytotoxic T lymphocytes, and IFN-γ production in the lung and splenocytes. A single dose of GXV induces a drastic reduction of viral titers.

9 Claims, 9 Drawing Sheets

OTHER PUBLICATIONS

Figure 1A:
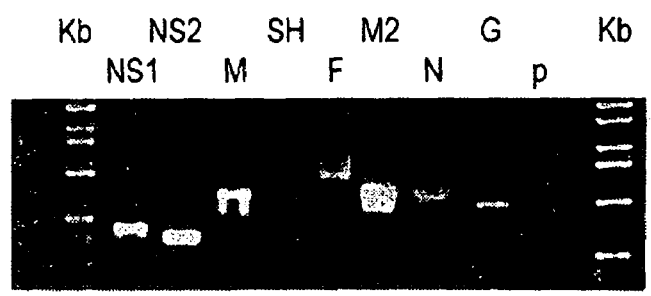

Matsuo et al., "Induction of Innate Immunity by Nasal Influenza Vaccine Administered in Combination with an Adjuvant (Cholera Toxin)", Vaccine, 2000, pp. 2713-2722.

Connors et al., "Respiratory syncytial virus (RSV) F, G, M2 (22K), and N proteins each induce resistance to RSV challenge, but resistance induced by M2 and N proteins is relatively short-lived", *J Virol* 65. 1634,1991.

Wyatt et al, "Priming and boosting immunity to respiratory syncytial virus by recombinant replication-defective vaccinia virus MVA", *Vaccine* 18:392, 1999.

Domachowske et al., "Respiratory syncytial virus infection: immune response, immunopathogenesis, and treatment," *Clin Microbiol Rev* 12:298, 1999).

Brandenburg et al., "Pathogenesis of RSV lower respiratory tract infection: implications for vaccine development," *Vaccine* 19:2769, 2001.

Groothuis et al., "Use of Intravenous Gamma Globulin To Passively Immunize High-Risk Children against Respiratory Syncytial Virus: Safety and Pharmacokinetics," *Antimicrobial Agents and Chemotherapy*, Jul. 1991, pp. 1469-1473.

Hemming et al., "Hyperimmune Globulins in Prevention and Treatment of Respiratory Syncytial Virus Infections," *Clin Microbiol Rev.* Jan. 1995;8(1):22-33. Review.

Li et al, "Plasmid DNA encoding the respiratory syncytial virus G protein is a promising vaccine candidate," *Virology*. Mar. 30, 2000; 269(1): 54-65.

Li et al, "Protection against respiratory syncytial virus infection by DNA immunization," *J Exp Med* Aug. 17, 1998;188(4):681-8.

Prince et al, "Efficacy and safety studies of a recombinant chimeric respiratory syncytial virus FG glycoprotein vaccine in cotton rats," *J Virol.* Nov. 2000;74(22): 10287-92.

Guy et al, "Design, characterization and preclinical efficacy of a cationic lipid adjuvant for influenza split vaccine," *Vaccine* 19:1794, 2001.

Anderson, L. "Respiratory syncytial virus vaccines for otitis media" *Vaccine*, 2001, 19:S59-S65.

Kumar, M. et al. "A RSV Genome Chitosan Nanosphere (RGCN) Vaccine Against Respiratory Syncytial Virus (RSV) Infection" *J. Allergy and Clin. Immuno.*, Feb. 2001, 2(107):S251 (abstract).

Whitehead, S. S. et al. "Recombinant Respiratory Syncytial Virus Bearing a Deletion of either the NS2 of SH Gene is Attenuated in Chimpanzees" *J. Virology*, Apr. 1999, 73(4):3438-3442.

Mao, H.Q. et al. "DNA-chitosan nanoshperes for gene delivery" in International Symposium on Controlled Release of Bioactive Materials, 23(1996), Kyoto, Japan, Controlled Release Society; abstract No. 4138, p. 401.

Mao, H.Q. et al. "DNA-chitosan nanospheres: derivatization and storage stability" in International Symposium on Controlled Release of Bioactive Materials, 24(1997), Stockholm, Sweden, Controlled Release Society, abstract No. 6016, p. 671.

Walsh, S.M. et al. "Combination of drug and gene delivery by gelatin nanospheres for the treatment of cystic fibrosis" in Proceedings of the International Conference on Controlled Release of Bioactive Agents, 24(1997), Stockholm, Sweden, abstract No. 238, p. 75.

Truong-Le, V.L. et al. "Delivery of DNA vaccine using gelatin-DNA nanospheres" In International Symposium on Controlled Release of Bioactive Materials, 24(1997), Stockholm, Sweden, Controlled Release Society, abstract No. 219, p. 39.

Roy, K. et al. "DNA-chitosan nanospheres: transfection efficiency and cellular uptake" in International Symposium on Controlled Release of Bioactive Materials, 24(1997), Stockholm, Sweden, Controlled Release Society, abstract No. 6017, p. 673.

Behera, A. et al. "Adenovirus-mediated interferon γgene therapy for allergic asthma: involvement of interleukin 12 and STAT4 signaling" *Human Gene Therapy*, 2002, 13:1697-1709.

Doolan, D. et al. "Utilization of genomic sequence information to develop malaria vaccines" *J. Exp. Biol.*, 2003, 206:3789-3802.

Dumonteil, E. et al. "DNA vaccines induce partial protection against *Leishmania mexicana*" *Vaccine*, 2003, 21:2161-2168.

Hellermann, G. and Mohapatra, S. "Genetic therapy: on the brink of a new future" *Genetic Vaccines and Therapy*, 2003, 1:1-2.

Kumar, M. et al. "Chitosan IFN-γ-pDNA nanoparticle (CIN) therapy for allergic asthma" *genetic Vaccines and Therapy*, 2003, 1:1-10.

Kumar, M.N.V.R. et al. "Cationic poly(lactide-co-glycolide) nanoparticles as efficient *in vivo* gene transfection agents" *J. Nanocsci. Nanotech*, 2004, 4(8):1-5.

Kumar, M.N.V.R. et al. "Cationic silica nanoparticles as gene carriers: synthesis, characterization and transfection efficiency *in vitro* and *in vivo* " *J. Nanosci. Nanotech.*, 2004, 4(7):1-6.

Kumar, M.N.V.R. et al. "Nanoparticle-mediated gene delivery: state of the art" *Expert Opin. Biol. Ther.*, 2004, 4(8):1-12 (author's proof; pp. 1213-1224 as published).

Kumar, M. et al. "Intranasal gene transfer by chitosan-DNA nanospheres protects BALB/c mice against acute respiratory syncytial virus infection" *Human Gene Therapy*, 2002, 13:1415-1425.

Kumar, M. et al. "Intranasal IFN-γgene transfer protects BALB/c mice against respiratory syncytial virus infection" *Vaccine*, 2000, 18:558-567.

Matsuse, H. et al. "Recurrent respiratory syncytial virus infections in allergen-sensitized mice lead to persistent airway inflammation and hyperresponsiveness" *J. Immunology*, 2000, 164:6583-6592.

Mohapatra, S. "Mucosal gene expression vaccine: a novel vaccine strategy for respiratory syncytial virus" *Pediatr. Infect. Dis. J.*, 2003, 22:S100-S104.

Moorthy, V. et al."Malaria vaccine developments" *The Lancet*, 2004, 363:150-156.

Muthumani, K. et al. "Issues for improving multiplasmid DNA vaccines for HIV-1" *Vaccine*, 2002, 20:1999-2003.

Ward, B.J. Vaccine adverse events in the new millennium: is there reason for concern? *Bulletin of the World Heath Organization*, 2000, 78(2):205-215.

Barends, M. et al. "Timing of Infection and prior immunization with respiratory syncytial virus (RSV) in RSV-enhanced allergic inflammation" *J Infections Diseases*, 2004, 189:1866-1872.

Bianco, I. et al. "Chitosan-induced phospholipase $A_2$ activation and arachidonic acid mobilization in $P388D_1$ macrohages" *FEBS Letters*, 2000, 466:292-294.

Centers for Disease Control and Prevention, 1999, Update: Respiratory syncytial virus activity—United States, 1998-1999 season.

Kneyber, M. et al. "Treatment and prevention of respiratory syncytial virus infection" *Eur. J. Pediatr*, 2000, 159:399-411.

Nicholas, J.A. et al. "Cytolytic T-lymphocyte responses to respiratory syncytial virus: Effector cell phenotype and target proteins" *j. Virology*, 1990, 64:4332-4241.

Openshaw, P. and Tregoning, J. "Immune responses and disease enhancement during respiratory syncytial virus infection" *Clin Mirobiol Rev*, 2005, 18:541-555.

Openshaw, P. et al. "Immunopathogenesis of vaccine-enhanced RSV disease" *Vaccine*2002, 20:S27-S31.

Otterlei, M. et al. "Characterization of binding and TNF-alpha-inducing ability of chitosans on monocytes: the involvement of CD14" *Vaccine*, 1994, 12:825-832, abstract.

Piedra, P. "Clinical experience with respiratory syncytial virus vaccines" *Pediatr Infect Dis J*, 2003, 22:S94-S99.

Richardson, S. et al. "Potential of low molecular mass chitosan as a DNA delivery system: biocompatibility, body distribution and ability to complex and protect DNA" *Intn'l J Pharmaceutics*, 1999, 178:231-243.

Bivas-Benita, M. et al. "Pulmonary delivery of chitosan-DNA nanoparticles enhances the immunogenicity of a DNA vaccine encoding HLA-A*0201-restricted T-cell epitopes of *Mycobacterium tuberculosis*" *Vaccine*, 2004, 22:1609-1615.

Dow, S. et al. "Systemic and local interferon γgene delivery to the lungs for treatment of allergen-induced airway hyperresponsiveness in mice" *Human Gene Therapy*, 1999, 10:1905-1914.

Hamajima, K. et al. "Chitin micro-particles (CMP): A useful adjuvant for inducing viral specific immunity when delivered intranasalty with an HIV-DNA vaccine" *Viral Immunology*, 2003, 16:541-547.

Hellerman, G. et al. "Chitosan IFN-gamma-gene nanosphere (CIN) therapy for allergic asthma: Modulation of specfic T-cell and dendritic cell responses" *J. Allergy Clin. Immunol.*, 2003, 111(2):S265, abstract No. 791.

Kong, X. et al. "Chitosan IFN-gamma-gene nanoparticle (CIN) therapy for allergic asthma in mice involves STAT4 signaling pathway" *J. Allergy Clin. Immunol.*, 2003, 111(2):S354, abstract No. 1144.

Kumar, M. et al. "Role of mucosal IFN-γ gene transfer on allergic sensitization and RSV Infection" *J. Allergy Clin. Immunol.*, 2002, 109(1):S4, abstract No. 78.

* cited by examiner

Oral vaccine does not induce AHR and is safe mRNA expression of several RSV genes following vaccination.

GENE EXPRESSION VACCINE

This application claims priority from U.S. Ser. No. 60/325,573, filed Sep. 28, 2001.

FIELD OF THE INVENTION

The invention relates generally to gene expression vaccines. More specifically, the invention relates to gene expression vaccines that can be administered intra-nasally or orally.

BACKGROUND

The respiratory syncytial virus (RSV) is the most common cause of viral lower respiratory tract infections in infants and children, affecting about 4 million children globally and leading to about 100,000 hospitalizations and 4,500 deaths per annum in the United States alone. RSV infection is associated with recurrent episodes of bronchiolitis, bronchial obstruction and exacerbation of asthma in children. Incidence of RSV infection-induced bronchiolitis has been increasing. There is no effective prophylaxis available against RSV infection. Previous attempts to develop a vaccine using a formalin-inactivated RSV vaccine not only failed but also exacerbated the disease when subsequent RSV infection occurred. (Chanock et al, Serious respiratory tract disease caused by respiratory syncytial virus: prospects for improved therapy and immunization, *Pediatrics* 1992; 90:137–43). Further, development of therapy against RSV has been limited by the short incubation period. Thus, development of an RSV vaccine has been a high priority at a global level.

Most of the RSV antigens are immunogenic in humans and mice, although the F and G antigens induce the majority of the neutralizing antibodies against RSV. (Connors, et al, Respiratory syncytial virus (RSV) F, G, M2 (22K), and N proteins each induce resistance to RSV challenge, but resistance induced by M2 and N proteins is relatively short-lived, *J Virol* 65.1634,1991; Wyatt et al, Priming and boosting immunity to respiratory syncytial virus by recombinant replication-defective vaccinia virus MVA. *Vaccine* 18:392, 1999). An analysis of the CTL repertoire in humans indicates that the N, SH, F, M, M2, and NS2 proteins are strong target antigens. Similarly, in BALB/c mice, the F, N, and especially the M2 proteins are shown to be the major target antigens of CTL activity. (Domachowske et al, Respiratory syncytial virus infection: immune response, immunopathogenesis, and treatment, *Clin Microbiol Rev* 12:298, 1999). Virus specific cytotoxic T lymphocytes play a major role in the clearance of RSV infection. Both serum and mucosal antibodies and MHC-class-I restricted cytotoxic T lymphocytes (CTLs) mediate protection against RSV infection. (Brandenburg et al, Pathogenesis of RSV lower respiratory tract infection: implications for vaccine development. *Vaccine* 19:2769, 2001). Previously, passive administration of neutralizing serum antibodies was shown to decrease the risk of RSV disease in animal models and in humans. (Groothuis et al, Use of intravenous gamma globulin to passively immunize high-risk children against respiratory syncytial virus: safety and pharmacokinetics. The RSVIG Study Group. *Antimicrob Agents Chemother.* 1991 July; 35(7): 1469–73; Hemming et al, Hyperimmune globulins in prevention and treatment of respiratory syncytial virus infections. *Clin Microbiol Rev.* 1995 January; 8(1):22–33. Review).

Vaccines studied to date comprise a subunit, peptide, or DNA vaccine made up of the RSV-F, -G and/or -M2 protein(s). Intramuscular injection of pDNA encoding the RSV-F or -G protein was effective in mice. (Li et al, Protection against respiratory syncytial virus infection by DNA immunization, *J Exp Med* 1998 Aug. 17; 188(4): 681–8; Li et al, Plasmid DNA encoding the respiratory syncytial virus G protein is a promising vaccine candidate, *Virology.* 2000 Mar. 30; 269(1): 54–65). In a cotton rat model, an F-G vaccine induced neutralizing antibody titers, which are 1–2 orders of magnitude lower compared to live RSV. (Prince et al, Efficacy and safety studies of a recombinant chimeric respiratory syncytial virus FG glycoprotein vaccine in cotton rats. *J Virol.* 2000 November;74(22): 10287–92). Immunization with plasmid DNAs (pDNA) expressing antigens in vivo that induce a protective cellular and humoral immune response is touted to have a number of advantages compared to other vaccines. However, the quantity of DNA used per unit bodymass and the route chosen might make these vaccines unsuitable for human use. (Guy et al, Design, characterization and preclinical efficacy of a cationic lipid adjuvant for influenza split vaccine, *Vaccine* 19:1794, 2001).

Currently, one of the options available to infants, who are at a high risk for developing RSV infection, is passive immunization at a monthly interval with a humanized antibody to the RSV-F antigen. Despite the inconvenience, expense, and partial effectiveness, passive immunization is often considered the only option, as a safe and effective vaccine against RSV is not available.

Therefore, a need remains for a DNA vaccine capable of mounting mucosal immunity against RSV. Given that infants of 2 to 6 months of age are among the most susceptible to RSV infection and that vaccination would preferably take place in the one month old infant, and given that a mucosal vaccine is considered more appropriate for developing a local immunity in these infants, who may have an immature local and systemic immune system, a mucosal RSV vaccine is preferred.

SUMMARY OF THE INVENTION

The present invention provides gene expression vaccine (GXV) comprising a cocktail of plasmid DNAs encoding corresponding RSV antigens in the form of chitosan nanospheres. In a first embodiment, the cocktail contains a combination comprising the F, G and at least one of the M, M2, SH, NS1, NS2, N, and P RSV antigens. In an alternative embodiment, the cocktail is a combination comprising the M2 and at least one of the F, G, M, SH, NS1, NS2, N, and P RSV antigens. In a further alternative embodiment, the cocktail contains a combination comprising the F, G, M2 and at least one of the M, SH, NS1, NS2, N, and P RSV antigens. The GXV is safe and effective against RSV, significantly attenuates pulmonary inflammation induced by RSV infection, and can be administered intra-nasally or orally. Not to be limited by theory, and although the precise cellular and molecular mechanisms for the effectiveness of GXV remain to be investigated, it is likely that the route, the combination of immunogenic antigens, and/or the conjugation with chitosan contribute to its effectiveness.

Accordingly, in a first embodiment, the invention is directed to a prophylactic mucosal vaccine against RSV infection.

In a further embodiment, the vaccine is developed using a RSV gene expression library formulated in the form of chitosan nanospheres for delivery via intranasal or oral route.

In a further embodiment, administration of the vaccine does not induce airway hyper-reactivity.

In a further embodiment a gene expression vaccine is provided having two distinct components: a pDNA cocktail conferring vaccine potency and chitosan conferring adjuvant activity.

In a further embodiment, the gene expression vaccine provides induced immunity to vaccine equivalent to that of live virus infection.

In a further embodiment the vaccine is effective at a single dose of approximately 25 μg of cocktail/mouse.

In a further embodiment the vaccine induces antibodies to multiple antigens, and preferably 9 antigens.

In a further embodiment, a method of making GXV vaccine is disclosed wherein the cDNAs for all RSV antigens except L antigen, are cloned in pVAX plasmid and the cocktail is coacervated with chitosan to formulate nanospheres.

In a further embodiment, the vaccine induces increases in specific IgG titers, nasal IgA titers, and enhances IFN-γ production in both lung as well as spleen tissues.

Other objects and advantages will become apparent to those skilled in the art from a review of the ensuing description, which proceeds with reference to the following illustrative drawings.

BRIEF DESCRIPTION OF FIGURES

FIGS. 1(A–B). FIG. 1A shows expression of RSV cDNAs following intranasal GXV vaccination; Lanes: Bp, marker and lanes marked as NS1, NS2, M, SH, F, M2, N, G and P refer to PCR corresponding to the RSV cDNAs. FIG. 1B shows expression of RSV cDNAs following intranasal GXV vaccination; immunoblot analysis. Lane Kd is a molecular weight marker; Lanes 1 and 2 are RSV infected and uninfected HEp-2 cell extracts.

FIGS. 2(A–C). FIG. 2A shows plaque forming unit of RSV from lungs of mice administered intranasally with PBS, naked DNA and GXV. FIG. 2B shows antigen load of RSV measured by ELISA from lungs of mice administered intranasally with PBS, naked DNA and GXV. FIG. 2C shows determination of methacholine responsiveness of mice administered intranasally with PBS, naked DNA and GXV measured by a whole-body plethysmograph. Methacholine responsiveness is measured as percent baseline enhanced pause (Penh).

FIGS. 3(A–C). FIG. 3A shows anti-RSV antibody response following GXV vaccination. BALB/c mice are intranasally administered with GXV vaccine (25 μg), naked DNA (25 μg), or PBS. Sera are collected from mice at 14 and 21 days after vaccination, and anti-RSV antibody titers measured by ELISA. FIG. 3B shows determination of RSV neutralizing antibody titers following vaccination. RSV suspension is incubated with various dilutions (0.01, 0.1 and 1) of sera and neutralization is carried out. FIG. 3C shows IgA antibody response following vaccination from nasal washes. Nasal washings (i.n) are collected from animals at 14 and 21 days after vaccination, and total IgA antibody levels measured by ELISA.

FIG. 4(A–B). FIG. 4A shows characterization of RSV specific CTLs induced by GXV vaccination. Mice are vaccinated with 25 μg of GXV, 25 μg naked DNA, or PBS. Three weeks later immune splenocytes are stimulated with persistently RSV infected fibroblast cell line BCH4. CTL activity is assessed in a standard 4-h $^{51}Cr$-release assay using uninfected BC cells and RSV-infected BCH4 fibroblast as targets. FIG. 4B shows determination of IFN-γ levels in BAL fluid. Groups of mice vaccinated as above are infected with RSV on day 16. BAL is performed on these mice on day 21, and IFN-γ levels are measured by ELISA. FIG. 4C shows determination of IFN-γ levels in splenocyte cultures. Groups of mice vaccinated as above are infected with RSV on day 16. Mice are sacrificed on day 21 and their spleenocytes are cultured in vitro on anti-CD3 antibody coated plates and IFN-γ levels in the culture supernatants are measured by ELISA.

FIG. 5. FIG. 5 shows mice vaccinated, as described earlier, and, on day 16, infected with RSV. Four days later, these mice are sacrificed, their lungs removed, and histological sections are stained with hematoxylin and eosin (HE). GXV vaccinated mice show less epithelium damage and cellular infiltration than the controls.

FIGS. 6(A–B). FIG. 6A shows expression of RSV cDNAs following intranasal RGCN vaccination. BALB/c mire are intranasally administered with a cocktail of RSV antigens cloned in the plasmid vector pVAX (GXV). Each mice inhales a total of 25 μg of cocktail DNA. Animals are sacrificed three days later after the last intranasal administration and RT-PCR is performed from total lung RNA. Expression of seven RSV mRNAs are shown. FIG. 6B shows that GXV alone does not induce airway hyperresponsiveness. BALB/c mice are orally administered with RGCN vaccine and 3 days later airway hyperresponsiveness is measured using whole body plethysmograph. Animals receiving GXV exhibit similar response to methacholine challenge when compared to animals receiving naked DNA or PBS alone (controls).

FIGS. 7(A–B). FIG. 7A shows anti-RSV antibody response following gRGCN vaccination. BALB/c mice are orally administered with GXV (25 μg), naked DNA (25 μg) alone or PBS. Sera are collected from animals at 14 and 21 days after the vaccination and anti-RSV antibody titers are measured by ELISA. Animals vaccinated with RGCN vaccine exhibit significantly higher antibody titers that controls. FIG. 7B shows IgA antibody response following RGCN vaccination. BALB/c mice are intranasally or orally administered with RGCN vaccine (25 μg), naked DNA (25 μg) alone or PBS. Fecal pellets (oral) and nasal washing (intranasal) are collected from animals at 14 and 21 days after the vaccination and total IgA antibody titers are measured by ELISA.

FIGS. 8(A–B). FIG. 8A shows expression of IFN-γ in spleen from oral and intranasal vaccinated mice. Mice receive RGCN vaccination orally and intranasally and infected with RSV on day 16. On day 21, animals are sacrificed and their spleens are cultured in vitro or BAL is performed. Expression from α-CD3 stimulated spleen cells; animals vaccinated orally produce more IFN-γ than intranasal group. FIG. 8B shows expression of IFN γ in BAL fluid from oral and intranasal vaccinated mice. Mice vaccinated intranasally show more IFN-γ production in their BAL fluid than the oral group.

FIG. 9. FIG. 9 shows oral GXV reduces pulmonary inflammation of the murine lung. BALB/c mice are orally administered with GXV or naked DNA (25 μg total). Animals are infected with RSV on day 16 and 4 days later (day 21) sacrificed. Lungs are removed and histological sections are stained with hematoxylin and eosin (HE). Representative photomicrographs are shown. Mice given the GXV show

DETAILED DESCRIPTION

A RSV gene expression library is constructed in pVAX plasmid and the library is coacervated with chitosan to formulate nanospheres, referred to herein as RGCN vaccine.

The present invention provides a gene expression vaccine (GXV) comprising a cocktail of plasmid DNAs encoding corresponding RSV antigens. The cocktail comprises combinations of the F, G, M, M2, SH, NS1, NS2, N, and P RSV antigens. The cocktail may contain a combination comprising the F, G and at least one of the M, M2, SH, NS1, NS2, N, and P RSV antigens. Alternatively, the cocktail may contain a combination comprising the M2 and at least one of the F, G, M, SH, NS1, NS2, N, and P RSV antigens. Also, alternatively, the cocktail may contain a combination comprising the F, G, M2 and at least one of the M, SH, NS1, NS2, N, and P RSV antigens. The GXV is formulated in the form of nanospheres with chitosan, a biodegradable, human-friendly, and cationic polymer that increases mucosal absorption of the vaccine without any adverse effects.

Chitosan allows increased bioavailability of the DNA because of protection from degradation by serum nucleases in the matrix and thus has great potential as a mucosal gene delivery system. Chitosan also has many beneficial effects, including anticoagulant activity, wound-healing properties, and immunostimulatory activity, and is capable of modulating immunity of the mucosa and bronchus-associated lymphoid tissue. GXV in the form of chitosan nanoparticles significantly induces specific neutralizing IgG antibody titers, and nasal IgA titers and IFN-γ levels in the lung compared to naked DNA controls. Chitosan increases the immunologic potency of GXV. However, the detailed mechanisms underlying chitosan potentiation of an antiviral immunity remain to be elucidated. It is to be noted that in addition to being very effective, GXV is safe, as demonstrated by a significant decrease in overall lung inflammation accompanied in vaccinated group compared to the non-vaccinated infected group and the lack of change in methacholine responsiveness between vaccinated and naive mice. This issue is extremely pertinent in view of the previous failure of the formalin-inactivated vaccine, which exacerbated the disease.

Vaccine induced humoral and cellular immunity is investigated. GXV significantly augments levels of both neutralizing serum and mucosal IgA antibodies compared to naked DNA-vaccinated and unvaccinated control groups. Although, the secreted IgA antibody provides protection for pathogens that enter via the mucosal route, the role of secretory IgA in protection against RSV is poorly understood. Without wishing to be bound by theory, it may be reasoned that because RSV is an obligatory intracellular mucosal pathogen affecting both the upper and lower respiratory tract, it is likely that mucosal IgA might provide protection against severe RSV disease by precluding its entry into mucosa and/or inhibiting the cell-cell syncytial spread of RSV.

GXV generates a significantly stronger CTL response compared to naked DNA and unvaccinated controls. These results, which are in agreement with other experimental vaccines, clearly support a role of vaccine-induced CTLs in virus clearance. Several studies indicate that the protective effect of CTL against cytopathic viruses is dependent on its production of cytokines such as IFN-γ. GXV significantly enhances the production of IFN-γ following vaccination, which may be useful in fighting RSV infection. IFN-γ has a direct antiviral effect and is particularly important in stimulating the cytolytic activity of natural killer (NK) cells and CD8+ cytotoxic T lymphocytes (CTL), which play a critical role in the control of RSV infection in a murine model and in humans.

In addition to the immunomodulatory activity of GXV, the possibility of inflammation induced by GXV is assessed by immunohistological analyses of lung sections. A semi-quantitative analysis of epithelial damage, and perivascular, peribronchial and interstitial infiltrating cells indicate that GXV significantly reduces cellular infiltration and epithelial damage compared to naked DNA and unvaccinated mice. The reason for the significant difference observed between naked DNA and GXV is unknown. Without wishing to be bound by theory, it is likely that GXV is less invasive, as a natural component of the mucosal system, compared to naked DNA. It is also possible that the accumulation of naked DNA in the epithelial submucosa due to reduced uptake by epithelial cells augments inflammatory response.

Collectively, our data demonstrates that GXV represents a novel vaccine concept against RSV infection, which at a single dose of only 1 mg/kg body weight is capable of decreasing viral titers by two orders of magnitude (100 fold) upon primary infection. The immunologic mechanisms for effectiveness of this vaccine include the induction of both high levels of serum IgG and mucosal IgA antibodies, the generation of an effective CTL response, and elevated lung-specific production of IFN-γ with anti-viral action. While as a single-dose vaccine GXV is extremely effective, it is conceived that dose escalation and prime-booster strategies might further enhance its effectiveness. In addition, GXV significantly decreases pulmonary inflammation and does not alter airway hyperresponsiveness, making it a safe vaccine.

The present invention provides an immunogenic composition for conferring protection in a host against disease caused by respiratory syncytial virus (RSV) comprising an F RSV antigen; a G RSV antigen; and at least one of M, M2, SH, NS1, NS2, N, or P RSV antigen. The present invention also provides an immunogenic composition for conferring protection in a host against disease caused by respiratory syncytial virus (RSV) comprising an M2 RSV antigen; and at least one of F, G, M, SH, NS1, NS2, N, or P RSV antigen. The present invention also provides an immunogenic composition for conferring protection in a host against disease caused by respiratory syncytial virus (RSV) comprising an F RSV antigen; a G RSV antigen; an M2 RSV antigen; and at least one of M, SH, NS1, NS2, N, or P RSV antigen. The immunogenic compositions of the present invention can be mucosal vaccines.

Materials and Methods

Animals

Six-week old female BALB/c mice are purchased from the Jackson laboratory (Bar Harbor, Me.) and maintained in pathogen free conditions at the animal center. All procedures are reviewed and approved by the University of South Florida and James A Haley VA Medical Center Committee on Animal Research.

Gene Construct, Generation of Chitosan Nanospheres and Gene Transfer

RSV cDNAs are amplified from the RSV-infected mouse lung cDNA library by polymerase chain reaction (PCR) using Vent polymerase (New England Biolabs, Beverly, Mass.) and cloned in the mammalian expression vector pVAX (Invitrogen, San Diego, Calif.). The resulting plasmids are propagated in *E. coli* DH5α cells. Large-scale plasmid DNA is prepared using a Qiagen kit (Qiagen, Chatsworth, Calif.), following the manufacturers specifications. This produces sufficiently pure DNA with minimum endotoxin contamination. pDNAs are mixed to make a cocktail of RSV cDNAs. DNA chitosan nanospheres are generated, as described by Roy, K., et al 1999, Oral gene delivery with chitosan—DNA nanoparticles generates immunologic protection in a murine model of peanut allegy, *Nat Med* 5:387. In the case of intranasal vaccination, mice are inoculated intranasally under light anesthesia with cocktail DNA chitosan nanospheres three times. Each mouse receives a total of 25 µg of total DNA complexed in the chitosan nanospheres. Control mice receive PBS and naked DNA.

Administration of Vaccine

Mice are administered intranasally (i.n.) with GXV (25 µg of total DNA/mouse) under light anesthesia. Control mice receive PBS or equivalent quantities of naked DNA. Sixteen days after vaccination, mice are infected intranasally with $1 \times 10^6$ pfu of the human RSV A2 strain (ATCC, Rockville, Md.) in a 50 µl volume. Five days post infection (p.i), mice are sacrificed, and their lungs and spleens are collected aseptically for RT-PCR, histopathological studies, cytokine, and viral plaque analyses. Mice are bled on days 14 and 21 post vaccination to obtain serum.

Viral Infection of Animals and Tissue and Serum Collection

On day 16 from the last vaccination, mice are infected intranasally with $1 \times 10^6$ pfu of human RSV A2 strain (ATCC, Rockville, Md.) in a 50 µl volume. On day 5 post infection (p.i.) mice are sacrificed and their lung and spleen collected aseptically. For RT-PCR, histopathological studies, cytokine and viral plaque analysis. Serum is collected from mice on days 14 and 21 following last vaccination.

Quantitation of RSV Titers and Antigen in Lung

To quantify RSV titers in the mouse lung, whole lungs are first weighed and then placed immediately in EMEM media supplemented with 10% FBS. Lungs are homogenized, followed by centrifugation at 10,000 RPM for 10 minutes at 4° C. Clear supernatant is collected and passed through a 0.45 µm methylcellulose filter (Gelman Sciences, Ann Arbor, Mich.). Serially diluted samples are used for plaque assay. Hep-2 cells growing on cover slips in 24 well plates (60–70% confluent) are overlaid with different dilutions of the lung homogenate and centrifuged at 1000 RPM for one hour. This leads to rapid adsorption of the virus into the cells. Cells are incubated in a $CO_2$ incubator at 37° C. for 24 hours. Following incubation, tissue culture medium are aspirated out and cells are washed twice with PBS. Cells are fixed with chilled absolute ethanol, dried and then are incubated with FITC-labeled anti-RSV polyclonal antibody (Light Diagnostics, Tennecula, Calif. for 30 in a humidified chamber. Cells are washed twice with the washing buffer (PBST, PBS+0.05% Tween-20, pH 7.4) and cover slips are mounted on the slide using fluoromount G (Southern Biotechnology Associates, Birmingham, Ala.). RSV plaques are enumerated under fluorescence microscope.

RNA Extraction and RT-PCR Analysis

Total cellular RNA is isolated from the lung tissue using TRIZOL reagent (Life Technologies, Gaithersburg, Md.), following the manufacturer's instructions. One ml of Trizol reagent is added to 50–100 mg of lung tissue and homogenized. Lung homogenate is suspended by pipeting and allowed to stand at room temperature for five minutes for lysis. Chloroform (200 µl) is added to each tube and mixed thoroughly. After five minutes, the cells are centrifuged at 12,000 rpm for 15 minutes at 15–20° C. The clear aqueous supernatant is transferred to a fresh tube and an equal volume of isopropanol is added, mixed well, and centrifuged at 12,000 rpm for 15 minutes at 15–20° C. The RNA pellet is washed with 70% ethanol, air dried and dissolved in diethyl-pyrcarbonate-treated water. RT-PCR is carried out for different RSV genes, as described by Behera, A. K. et al, 2001, Blocking Intercellular Adhesion Molecule-1 on Human Epithelial Cells Decreases Respiratory Syncytial Virus Infection, *Biochem Biophys Res Comm* 280:188.

Pulmonary Function

To assess the pulmonary function in vaccinated and control groups, mice are vaccinated with GXV. Three days later, airway responsiveness (i.e., bronchoconstriction) is assessed non-invasively in conscious, unrestrained mice with a whole body plethysmograph (Buxco Electronics, Troy, N.Y.), as described by Matsuo K. et al, 2000, Recurrent respiratory syncytial virus infection in allergen sensitized mice lead to persistent airway inflammation and hyperresponsiveness, *J. Immunol* 164:6583. With this system, the volume changes that occur during a normal respiratory cycle are recorded as the pressure difference between an animal containing chamber and a respiratory reference chamber. The resulting signal is used to calculate respiratory frequency, minute volume, tidal volume, and enhanced pause (Penh). Penh is used as the measure of bronchoconstriction and is calculated from the formula: Penh=pause ×(peak expiratory pressure/peak inspiratory pressure), where pause is the ratio of time required to exhale the last 30% of tidal volume relative to the total time of expiration. Mice are placed in the plethysmograph and the chamber is equilibrated for 10 minutes. They are exposed to aerosolized PBS (to establish a baseline) followed by incremental doses (6, 12.5, 25 and 50 mg/ml) of methacholine (Sigma Chemicals, St. Louis, Mo.). Each dose of methacholine is aerosolized for five minutes, and respiratory measurements are recorded for five minutes afterward. During the recording period, an average of each variable is derived from every 30 breaths (or 30 seconds, whichever occurs first). The maximum Penh value after each dose is used to measure the extent of bronchoconstriction.

Bronchoalveolar Lavage (BAL), Spleen Cell Culture and Assay for IFN-γ

Bronchoalveolar lavages are performed on vaccinated and control mice. Mice are sacrificed on day five post infection by an overdose injection of pentobarbital (Nembutal (Abbot Laboratories, North Chicago, Ill.)), (0.6 g/kg) i.p. and the thorax is opened. The lung vascular bed is flushed with two to three ml of chilled saline. The trachea is exposed and canulated with a 26 G needle connected to a tuberculin syringe. The lung is then lavaged thrice with 0.5 ml of PBS and the bronchioalveolar lavage fluid (BALF) is pooled. Recovered BAL fluid volumes range between 75 and 85% of instilled PBS. There is no statistically significant difference in recovered BAL fluid volumes between control and experimental groups. Supernatant is collected following centrifugation of the BAL and stored at −70° C. until it is assayed for cytokines.

For spleen cell culture, single-cell suspensions are prepared from the spleens of BALB/c mice and cultured in wells coated with anti-CD3 Abs (1 µg/ml; clone 17A2, PharMingen, San Diego, Calif.). IFN-γ was assayed from BALF and 24-h culture supernatant using an ELISA kit (R&D Systems, Minneapolis, Minn.).

Assay for Total IgA Antibodies

IgA antibodies are collected from the nasal washes as described by Matsuo K, et al 2000, Induction of innate immunity by nasal influenza vaccine administered in combination with an adjuvant (cholera toxin), *Vaccine,* 18:2713. A syringe needle is inserted into the posterior opening of the nasopharynx and a total of one ml of phosphate-buffered saline (PBS) containing 0.1% bovine serum albumin (BSA) is injected into the opening three times; the out flow is collected as the nasal wash. The nasal wash is centrifuged to remove cellular debris and used for Ab assay. For total IgA antibody assays, ELISA plates are coated overnight at 4° C. with 200 ng/well of anti-mouse IgA antibody (02271D, Pharmingen, San Diego, Calif.). After three washes, samples are added and incubated at room temperature for 2 hours. Following another wash, biotinylated anti mouse IgA (556978, Pharmingen, San Diego, Calif.) antibody is added and the plates are incubated for another 2 hours. Following three washes, avidin peroxidase conjugate (1:10,000, Sigma Chemicals, St. Louis, Mo.) is added and plates are incubated for another hour. Color is developed after the addition of the substrate Tetramethyl benzidine (Pharmingen, San Diego, Calif.) and absorbance is read at 450 nm using an automated-ELISA reader.

Anti-RSV Antibody Assay

To quantitate anti RSV antibody titers, ELISA plates are coated overnight at 4° C. with purified RSV (200 ng/well). Plates are washed and blocked with blocking buffer (1% BSA in PBS, pH 7.4) for one hour at 37° C. Samples are added to the plate and incubated at 37° C. for 2 hours. Plates are washed again and anti-mouse IgG peroxidase conjugate is added at a dilution of 1:10,000 (Boehringer Manheim, Germany) and incubated for 1 hour. Following three washes, substrate is added and color is allowed to develop for 20–30 minutes. Absorbance is read at 450 nm using an automated ELISA reader.

Virus Neutralization Assay

Different dilutions of serum obtained at day 14 are mixed with 100 µl of RSV inoculum and incubated at 37° C. for one hour. This is used to infect HEp-2 cultures growing in 48-well culture plates. RSV titer is determined.

Immunoblotting

Thirty microgram of RSV infected HEp-2 cell extract is fractionated on a 4–20% gradient SDS-PAGE and transferred to the nitrocellulose membrane. The membrane is blocked with blocking buffer (5% w/v non-fat dry milk in TBS-0.1% Tween 20, pH 7.6) and incubated overnight at 4° C. with a 1:250 dilution of pooled serum from various groups of immunized mice. The membrane is washed four times in washing buffer (TBS-0.1% Tween-20, pH 7.6) and incubated with anti-mouse IgG peroxidase conjugate for 1 h at room temperature. Following four more washes, the blot is developed by the addition of ECL chemiluminescent detection reagents (0.125 ml/cm$^2$), according to the manufacturer's instructions (Amersham Life Sciences, Arlington Heights, Ill.).

Histology and Scoring for Airway Inflammation

Lungs are inflated with intratracheal injections of PBS followed by 10% neutral buffered formalin solution (Sigma Chemicals, St. Louis, Mo.) to preserve the pulmonary architecture in an expanded state. Lungs are transferred to 80% ethanol after one hour and then embedded in paraffin. The sections are stained with hematoxylin and eosin. A semi-quantitative evaluation of inflammatory cells in the lung sections, including alveolar spaces, bronchovascular bundles and interstitium, is performed. Inflammatory infiltrates are assessed morphologically for location, thickness, and cell composition.

CTL Studies

Splenocytes ($2.5 \times 10^6$ cells/mL) from mice immunized with the PBS, GXV, and naked DNA are incubated in complete RPMI containing 10 U/mL IL-2 and $2.5 \times 10^6$ cells/mL of persistently RSV-infected mitomycin (Sigma, St Louis, Mo.) treated fibroblasts (BCH4 cells). Cultures are tested on day 6 for antigen-specific lysis by adding varying numbers of effector cells to $^{51}$Cr-labeled syngeneic fibroblasts either persistently RSV-infected (BCH4) or uninfected (BC) target cells ($1 \times 10^4$). After 5 h of incubation at 37° C., cell supernatants are harvested for the determination of $^{51}$Cr in a gamma counter. The percentage of specific lysis is calculated as [(experimental cpm—spontaneous cpm)/(total cpm—spontaneous cpm)]×100. Spontaneous release and total release are determined from target cells incubated with medium alone or after the addition of 2.5% Triton X-100, respectively.

RESULTS

Mucosal GXV Vaccination is Safe and Effective

To determine the expression of RSV antigens in the lung following intranasal administration of the plasmid cocktail, the expression is measured for all cDNAs at the mRNA level by RT-PCR. The mRNA expression is detectable for seven of the nine plasmids including NS1, NS2, M, SH, F, M2 and N. All of the mRNAs are of exected size. There is a qualitative difference in expression of different mRNAs. These results indicate that intranasally administered plasmids readily express the encoded antigen in the lung cells.

A major concern with RSV vaccine is the enhancement of inflammation. To test whether the intranasal administration of GXV vaccine induces airway hyperreactivity the percentage baseline enhanced pause (Penh) is measured in three groups of animals including the PBS control and animal vaccinated with either naked plasmid cocktail or GXV vaccine. Animals receiving GXV vaccine exhibit similar response to methacholine challenge when compared to animals receiving naked DNA or PBS alone (controls). These results suggest that the GXV vaccine does not induce airway hyperreactivity.

To measure the effect of vaccine, BALB/c mice are intranasally administered with GXV vaccine or naked DNA. Animals are infected with RSV on day 16 and four days later (day 21) sacrificed. Lungs are removed and their homogenates are used for RSV plaque assay. Mice vaccinated with the GXV vaccine show a significant reduction in RSV titers (two to three fold) when compared to PBS control and naked DNA cocktail. A reduction in the viral titers of the lung is considered to be gold standard in judging the effectiveness of a vaccine. These results indicate that chitosan increases the potency of pDNA vaccine and that GXV provides an effective vaccine against RSV infection.

GXV Reduces RSV Infection-induced Pulmonary Inflammation

Lung inflammation is examined in groups of mice receiving GXV vaccine, and the naked plasmid DNA cocktail and these are compared with control mice treated with saline. The group of mice receiving GXV vaccine show less epithelial damage, mononuclear cell (MNC) and polymorphonuclear cell (PMNC) infiltrates in the interstitial and peribronchovascular region as compared to the naked plasmid vaccinated group and control. The PBS group is similar in lung histology to the normal uninfected mice and the naked DNA vaccination exhibit disruption of the epithelium, whereas GXV vaccinated mice show a lung phenotype comparable to the normal mice. These results suggest that GXV vaccine protects mice from RSV infection induced pulmonary inflammation.

GXV Induces an Anti-rsv Antibody Response

To determine whether the mucosal administration of GXV vaccine induces specific antibodies in mice, the RSV specific antibody titers are measured in mice administered with either the naked plasmid cocktail or GXV vaccine. Animals vaccinated with GXV vaccine exhibit significantly higher antibody titers than controls. The secreted IgA antibody is considered to be protective for mucosal pathogens as the nose is the main site of entry for RSV. The levels of total IgA antibodies in nasal wash are measured to verify if this class of antibody is changed as a result of vaccination. Animals vaccinated with GXV vaccine exhibit significantly higher IgA antibody titers than controls. These results indicate that GXV vaccine induce secretion of antibodies in the serum and specifically the IgA.

GXV Induces Expression of IFN-γ in the Lung and Spleen

IFN-γ is a major anti-viral cytokine, thus for a vaccine to be effective, it must induce IFN-γ expression. To examine if GXV vaccine induces IFN-γ expression, mice are administered with GXV vaccine and then infected with RSV on day 16. On day 21, animals are sacrificed, a bronchioalveolar lavage is performed and their spleenocytes are cultured in vitro. GXV vaccinated mice exhibit significantly more IFN-γ production in their BAL fluid than the controls. Also, cultured spleen cells stimulated with anti-CD3 antibody for mice vaccinated with GXV show more IFN-γ production than the controls.

Statistical Analysis

Figure 2A:
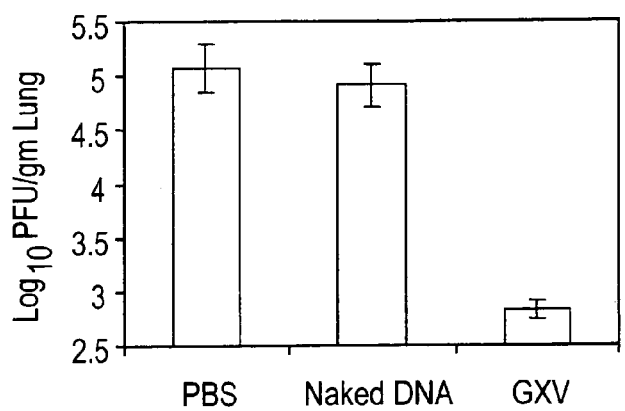
Figure 2B:
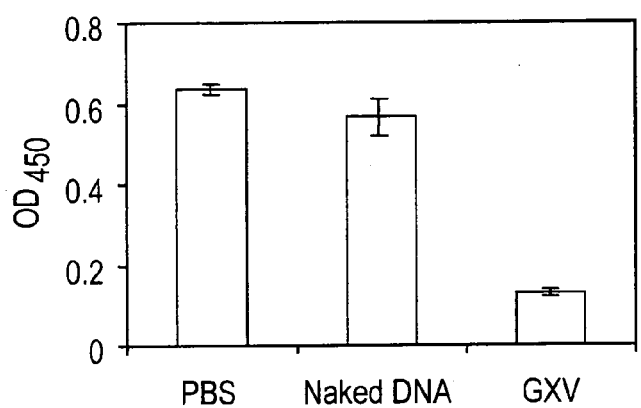
Figure 2C:
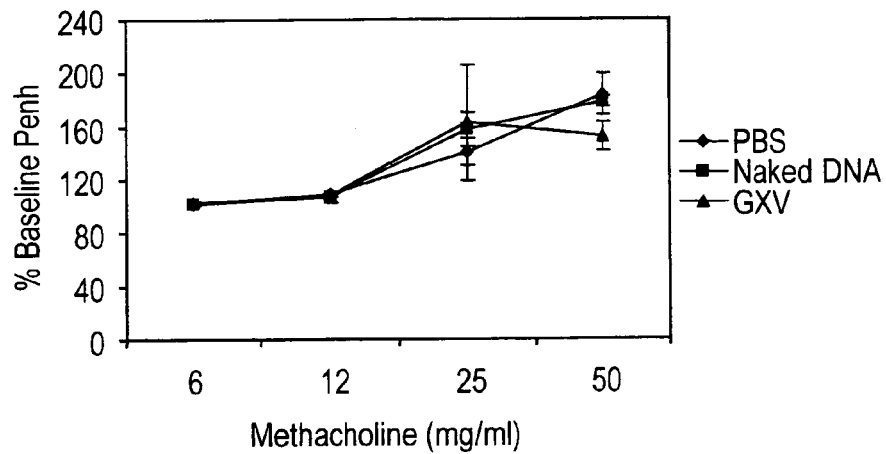

Pairs of groups are compared by the student's t-test. Differences between groups are considered significant at $p<0.05$. Values for all measurements are expressed as the mean±SD. The data is shown in Table 1. Each value in Table 1 represents the mean±SD of 5 fields from 6 individual lung sections from each mouse in a group (n=4). Statistical group of mice show that vaccinated mice exhibit more than a substantial decrease in antigen load (77%) when compared to PBS controls, FIG. 2B. These results indicate that chitosan increases the potency of pDNA vaccines and that GXV provides an effective vaccine against RSV infection. To test whether the intranasal administration of GXV induces airway hyperreactivity, the % baseline enhanced pause (Penh) is measured in all the three groups of animals. Animals receiving GXV exhibit a similar response to methacholine challenge when compared to animals receiving naked DNA or PBS alone (controls) FIG. 2C. These results suggest that the GXV treatment by itself does not induce any significant change in airway hyperreactivity.

Figure 3A:
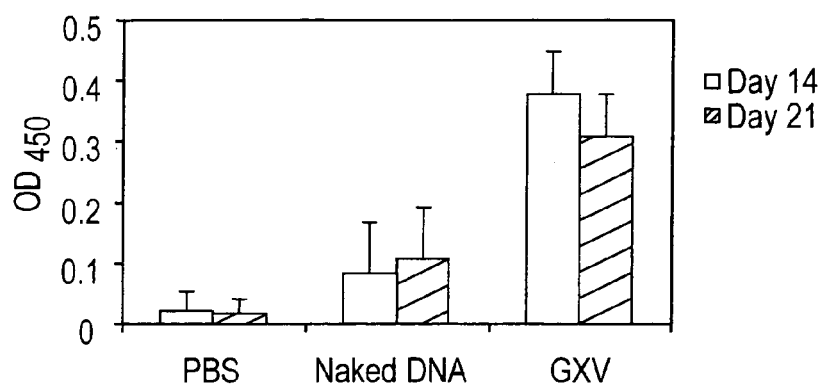
Figure 3B:
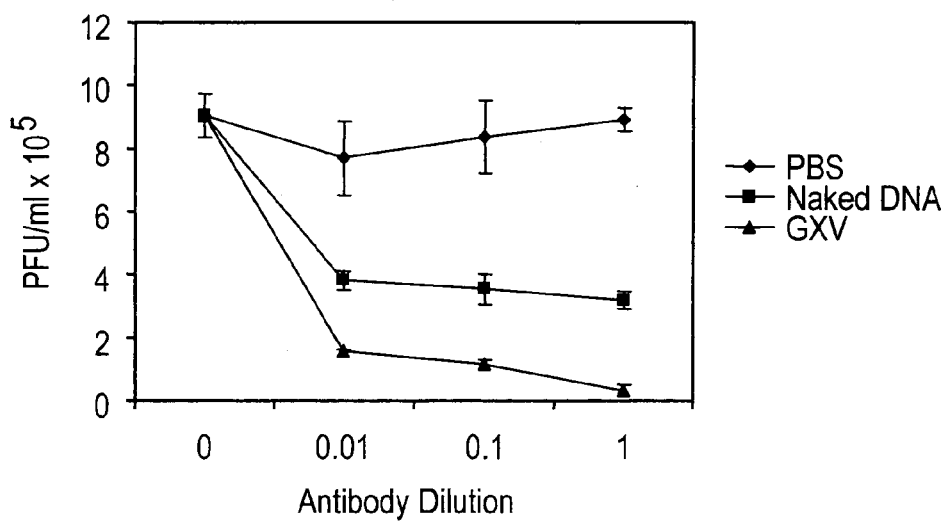
Figure 3C:
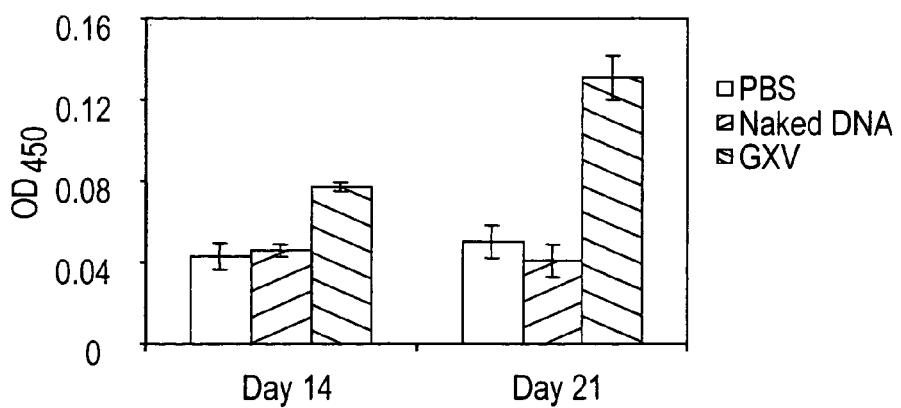
Figure 4A:
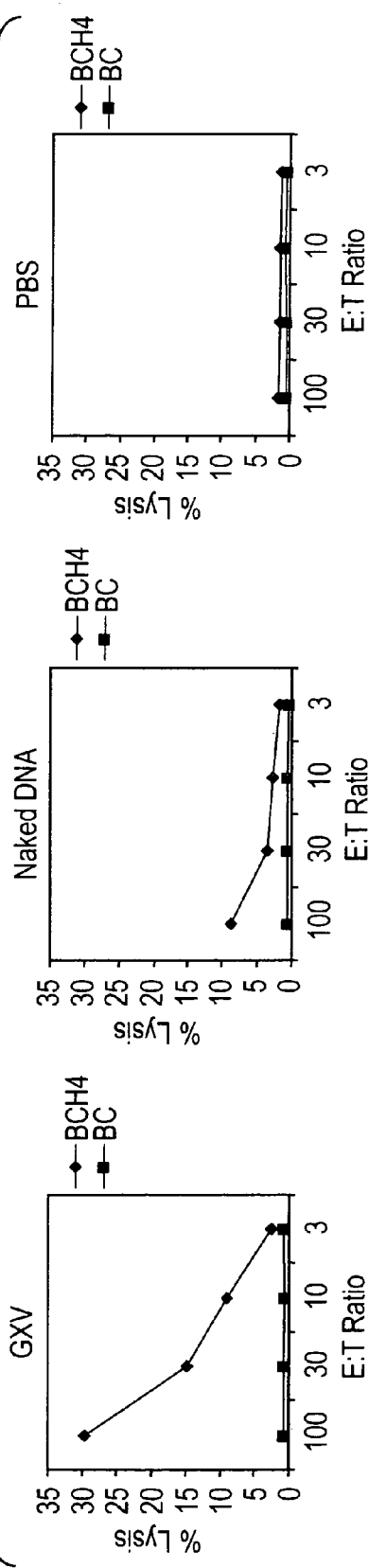
Figure 4B:
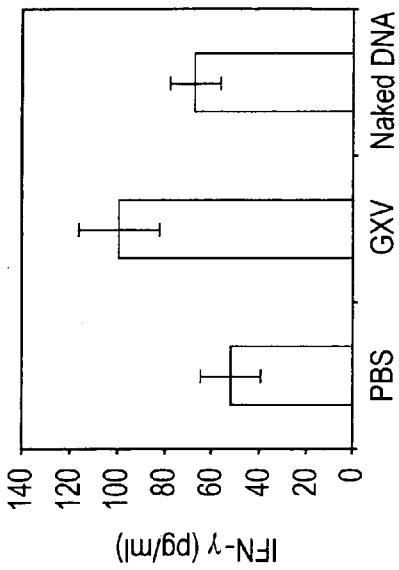
Figure 4C:
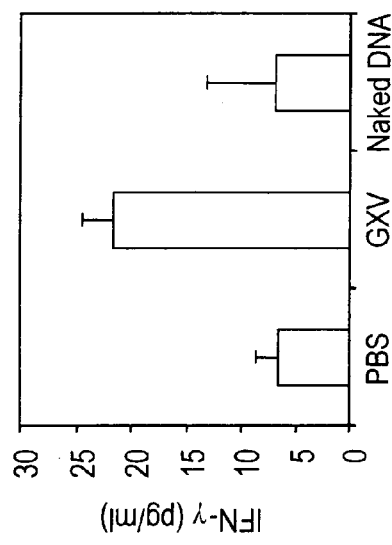

Both serum and mucosal responses are important ingredients of an effective vaccine. The secreted IgA antibody is considered to be protective for mucosal pathogens, as the nasal passage is the main site of entry for RSV. GXV given intranasally induces specific antibodies in mice, RSV-specific antibody titers are measured in mice administered with either the naked plasmid cocktail or GXV. Animals vaccinated with GXV exhibited significantly higher serum antibody titers than controls FIG. 3A. Incubation of RSV with the serum obtained from vaccinated mice reduces virus infection of HEp-2 cells, indicating the production of neutralizing antibodies following vaccination FIG. 3B. GXV mice show significantly higher neutralizing titers compared to mice given naked DNA, both of which are significantly different from the control group. The levels of total IgA antibodies in nasal wash measured verify that this class of antibody was changed as a result of vaccination with GXV. Animals vaccinated with GXV exhibit significantly higher IgA antibody titers than controls FIG. 3C. These results indicate that GXV induces the increased production of neutralizing antibodies in serum and nasal IgA. Differences are indicated as: a; $P<0.05$, aa; $P<0.01$ and aaa; $P<0.001$ compared to PBS control; b; $P<0.05$ compared to naked DNA control.

TABLE 1

| Pathology | Semi-quantitative analysis: | | |
| --- | --- | --- | --- |
|  | PBS | Naked DNA | GXV |
| Epithelial Damage | 2.53 ± 0.17 | 2.25 ± 0.30 | 1.4 ± 0.52[aab] |
| Interstitial-alveolar infiltrate | 2.66 ± 0.21 | 2.36 ± 0.33 | 1.76 ± 0.35[aaa] |
| Peribronchovascular infiltrate | 2.01 ± 0.20 | 1.81 ± 0.57 | 1.46 ± 0.23[a] |

Figure 1B:
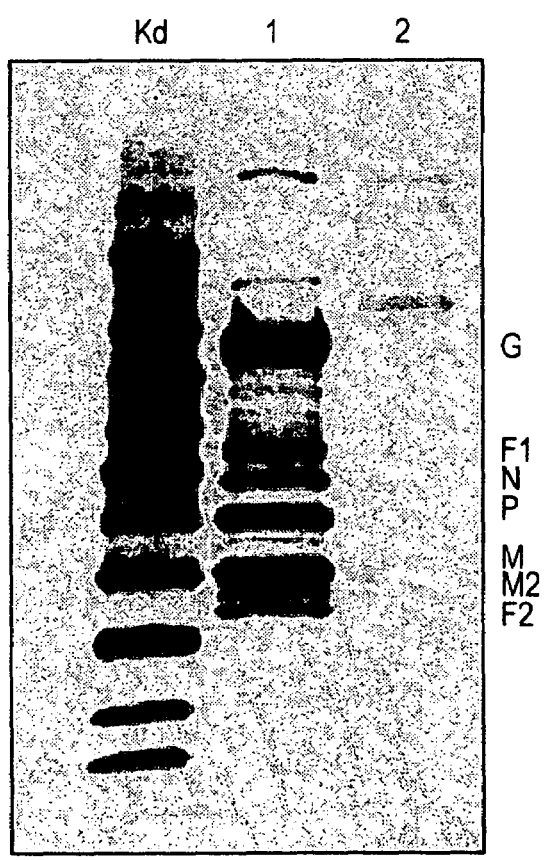

GXV administered intra-nasally results in the efficient expression of constituent RSV antigens, the lung tissues of mice are examined using RT-PCRs and western blot analyses. The results of an RT-PCR analysis from the lung mRNA of a given GXV shows that all of the mRNAs encoded by the GXV are detectable in the lung tissue, FIG. 1A. Evidence that these mRNAs are translated to produce sufficient immunogens is obtained by using a pooled sera (n=4) of these mice, which reacts with a number of RSV antigens present in RSV-infected HEp-2 cell supernatant in a western blot analysis FIG. 1B. These results indicate that GXV induces the production of RSV antigens, which elicit an antibody response.

Mice are administered a single dose of either GXV (a total of 25 μg of DNA) or naked DNA in saline (control). Analysis of lung virus titers following acute, live RSV infection shows a significant (100-fold) reduction in RSV titers in GXV mice compared to PBS controls FIG. 2A. Mice administered naked DNA show titers similar to those of the PBS group, suggesting naked DNA is not effective when administered via the intranasal route. Examination of total RSV antigen load in the vaccinated and control GXV vaccinated mice are analyzed for the presence of splenic, RSV-specific CTL using persistently RSV-infected BCH4 as the target and RSV-negative BC cells as the control. PBS or naked DNA controls does not elicit a detectable CTL response. In contrast, mice immunized with GXV generated CTL responses FIG. 4A, and these CTLs are shown to be $CD8^+$ and MHC class I-restricted (data not shown). IFN-γ is considered to be the major anti-viral cytokine. Thus, in order for a vaccine to be effective, it must induce IFN-γ expression. IFN-γ is assayed from the cultured spleen cells and broncho-alveolar lavage (BAL) of GXV vaccinated and control groups of mice. GXV vaccinated mice exhibit significantly more IFN-γ production in their BAL fluid than the controls FIG. 4B. Cultured spleen cells stimulated with anti-CD3 antibody for mice vaccinated with GXV show more IFN-γ production than the controls FIG. 4C.

Figure 5:
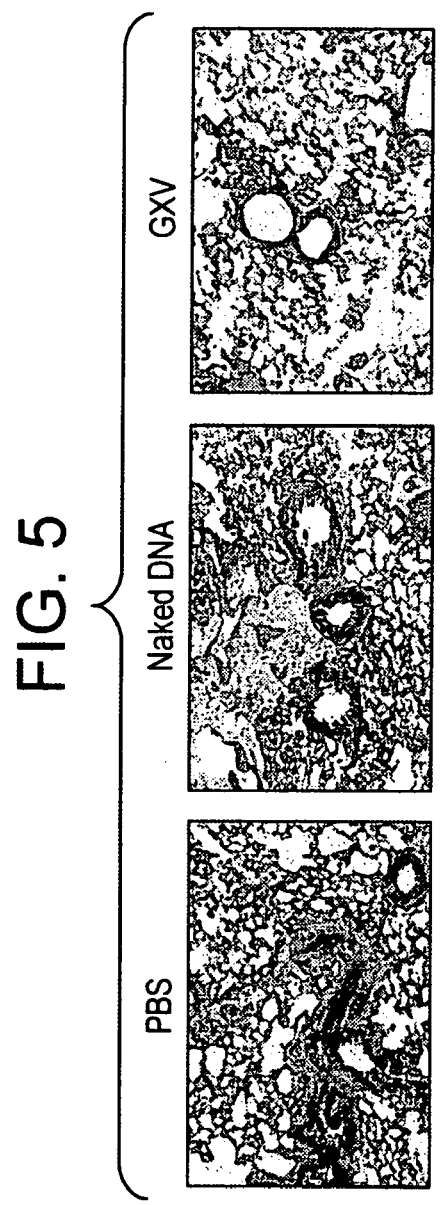
Figure 6B:
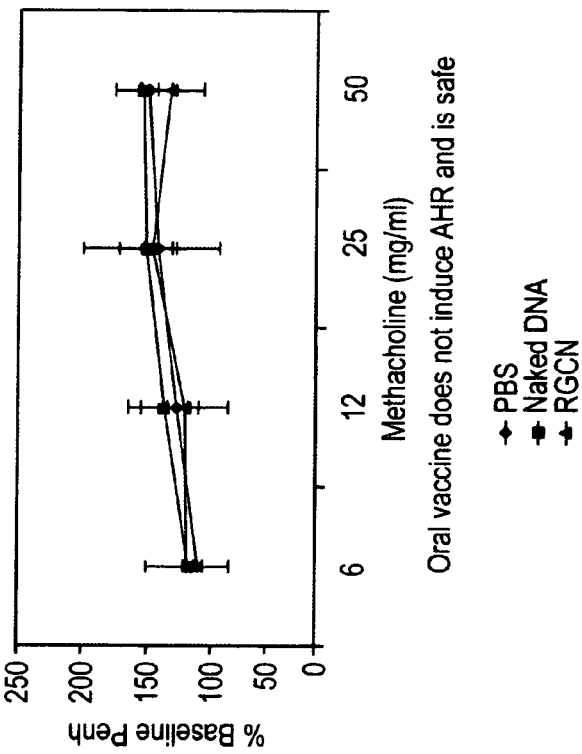
Figure 6A:
Figure 7B:
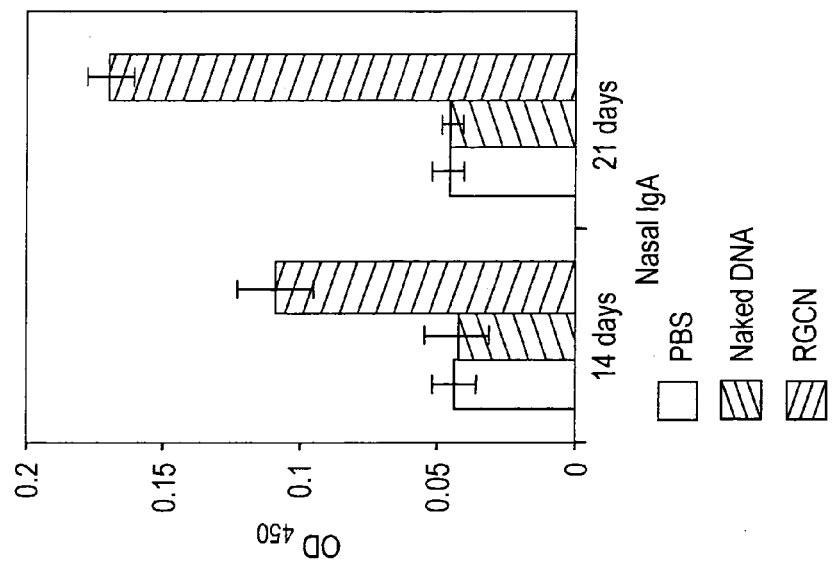
Figure 7A:
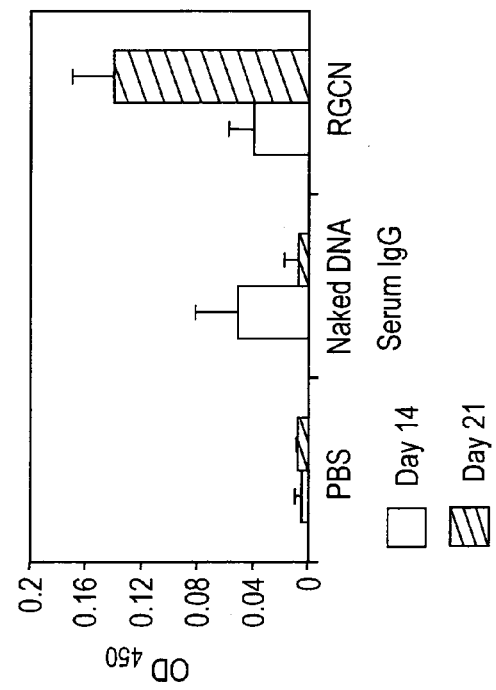
Figure 8B:
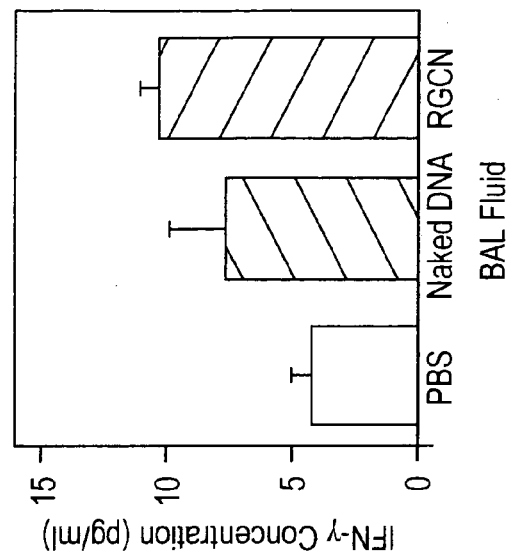
Figure 8A:
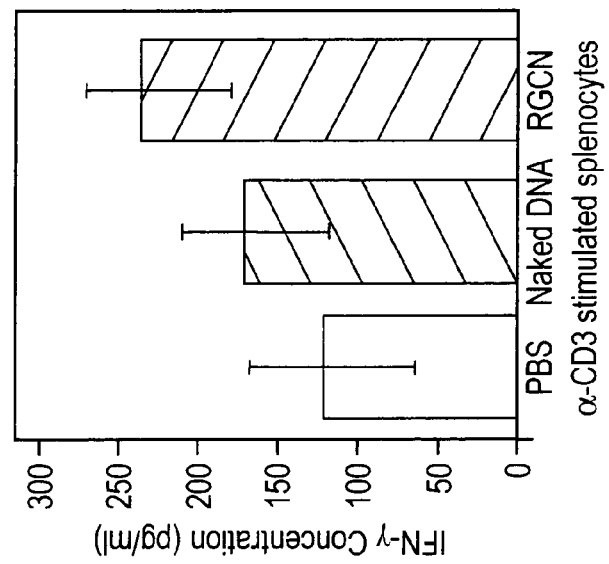
Figure 9:
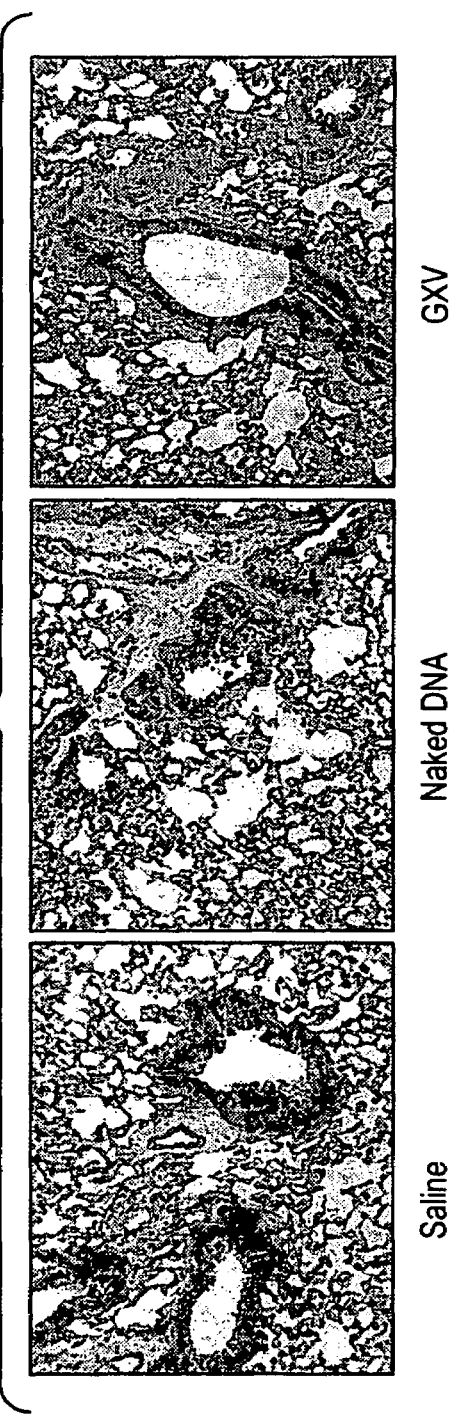

Lung inflammation is examined in different groups of mice. Representative pathological features are shown in FIG. 5A. The group of mice that received the GXV vaccine exhibit less epithelial damage, mononuclear cell (MNC), and polymorphonuclear cell (PMNC) infiltrates in the interstitial and peribronchovascular region, as compared to controls FIG. 5. The PBS group and the naked DNA group exhibit disruption of the epithelium, whereas GXV vaccinated mice showed a lung phenotype comparable to normal mice (data not shown). These results suggest that the GXV vaccine protects mice from RSV infection-induced pulmonary inflammation. A semi-quantitative analysis using a scoring system for inflammation in the lung is shown in Table I. Groups of mice that received GXV vaccine exhibited reduced epithelial damage ($P<0.01$, compared to PBS and $P<0.05$; compared to naked DNA) and pulmonary inflammation compared to naked DNA and PBS controls. The group of mice that receive GXV exhibited reduced ($P<0.01$) interstitial alveolar infiltrate and peri-bronchovascular infiltrate ($P<0.05$) when compared to the PBS control. No statistically significant difference is found with the naked DNA control group. These results suggest that GXV protects mice from RSV infection-induced pulmonary inflammation.

Throughout this application, various publications, have been referred to. The disclosures of these publications in their entireties are hereby incorporated by reference into this application to more fully describe the state of the art to which this invention pertains.

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

What is claimed is:

1. An immunogenic composition comprising nanospheres, wherein said nanospheres comprise plasmid DNA coacervated with chitosan, wherein said plasmid DNA encode respiratory syncytial virus (RSV) antigens M2, F, G, M, SH, NS1, NS2, N, and P, and wherein said plasmid DNA are expressed in vivo, thereby producing each of said RSV antigens.

2. A method for raising an immune response in a host against RSV, comprising administering to the host an immunoeffective amount of the immunogenic composition of claim 1.

3. The method of claim 2, wherein said administering is oral or intranasal.

4. The method of claim 2, wherein said administering does not induce airway hyperreactivity.

5. The method of claim 2, wherein the immunoeffective amount is administered in a single dose.

6. The method of claim 2, wherein the immunoeffective amount is about 1 mg/kg host weight.

7. A method of making the immunogenic composition of claim 1, comprising coacervating the plasmid DNA with chitosan to form the nanospheres.

8. The method of claim 7, further comprising cloning cDNA encoding the RSV antigens in plasmids to form the plasmid DNA.

9. An immunogenic composition comprising nanospheres, wherein said nanospheres comprise plasmid DNA coacervated with chitosan, wherein said plasmid DNA encode respiratory syncytial virus (RSV) antigens M2, F, G, M, SH, NS1, NS2, N, and P, wherein said immunogenic composition is an inhalant, and wherein said plasmid DNA are expressed in vivo, thereby producing each of said RSV antigens.

* * * * *

UNITED STATES PATENT AND TRADEMARK OFFICE
CERTIFICATE OF CORRECTION

PATENT NO. : 7,118,888 B2
APPLICATION NO. : 10/073065
DATED : October 10, 2006
INVENTOR(S) : Shyam Mohapatra et al.

It is certified that error appears in the above-identified patent and that said Letters Patent is hereby corrected as shown below:

Title page, item (75):
"Inventors: Shyam S. Mohapatra, Tampa, FL (US); Mukesh Kumar, Norwood MA (US); Shua-ku Huang, Towson, MD (US); Kam Leong, Ellicott City, MD (US)" should read --Inventors: Shyam S. Mohapatra, Tampa, FL (US); Mukesh Kumar, Norwood MA (US); Shua-ku Huang, Towson, MD (US); Kam Leong, Ellicott City, MD (US); Aruna K. Behera, Watertown, MA (US); Li-Chen Chen, Taipei (TW); Cristina Perez de la Cruz, Bowie, MD (US)--.

Column 11,
Line 12, "Anti-rsv" should read --Anti-RSV--.

Signed and Sealed this

Nineteenth Day of May, 2009

JOHN DOLL
*Acting Director of the United States Patent and Trademark Office*